United States Patent [19]

Kojima et al.

[11] Patent Number: 5,502,181
[45] Date of Patent: Mar. 26, 1996

[54] LOW GEL STRENGTH AGAR-AGAR

[75] Inventors: Masaaki Kojima; Kazuhiro Tabata; Yuji Uzuhashi; Yoshiki Ito, all of Nagano, Japan

[73] Assignee: INA Food Industry Co., Ltd., Nagano, Japan

[21] Appl. No.: 324,545

[22] Filed: Oct. 18, 1994

Related U.S. Application Data

[62] Division of Ser. No. 6,277, Jan. 19, 1993, abandoned.

[30] Foreign Application Priority Data

| May 15, 1992 | [JP] | Japan | 4-148855 |
| Jul. 23, 1992 | [JP] | Japan | 4-217250 |
| Aug. 3, 1992 | [JP] | Japan | 4-226398 |

[51] Int. Cl.$^6$ .................................................. C08B 37/12
[52] U.S. Cl. ........................ 536/123.1; 536/124; 536/128; 426/575
[58] Field of Search ........................... 536/3, 124, 123.1, 536/128; 426/575

[56] References Cited

PUBLICATIONS

Derwent Abstract of JP8805051 (Aug. 1988) Chuo Giken Kogyo KK.
Guisely "The Relationship Between Methoxyl Content and Gelling Temperature of Agarose" Carbohydrate Research, 13 (1970) p. 247–256.

*Primary Examiner*—Jeffrey Mullis
*Attorney, Agent, or Firm*—Lowe, Price, Leblanc & Becker

[57] ABSTRACT

According to a low gel strength agar of the invention, the molecules of agar are cut to short fragments, and the gel strength of the agar is adjusted to be 250 g/cm$^2$ or below at 1.5 % agar concentration. Thus, even when the agar is used at a certain agar concentration or above, a soft gel having a low gel strength with no syneresis can be obtained. When the agar is contained in foods or cosmetics, special advantages, which are not obtainable with prior-art products, can be achieved.

10 Claims, 5 Drawing Sheets

SOLUTION  DOUBLE HELIX  ASSOCIATION

LOW GEL STRENGTH AGAR-AGAR

This application is a division of application Ser. No. 08/006,277 filed Jan. 19, 1993 now abandoned.

BACKGROUND OF THE INVENTION

1. Field of the Invention

The present invention relates to low gel strength agar-agar or agar which has a low gel strength and does not coagulate at normal temperatures.

2. Description of the Related Art

Gelling agents include gelatin, starch, carrageenan, and agar. Of these, the agar, which can produce stickiness-free gel with crispy texture, is made from red algae including Gelidium and Gracilaria. The agar has special properties, unlike other gelling agents, and is applicable to various uses.

One of parameters showing the properties of agar is gel strength which indicates the solidity of gel. In general, the gel strength is proportional to the agar concentration in a solution. Thus, if agar with high gel strength is used, a gel with desired solidity can be obtained with a small amount of such agar. Under the circumstances, there is a trend in which agar with high gel strength is developed.

The gel strength of normal agar is 400 $g/cm^2$ or above in the case of powdered agar or flaked agar manufactured by industrial processes, and is 250 to 400 $g/cm^2$ in the case of square agar or strip agar.

The gel strength is measured in the following manner. A solution containing 1.5% of agar, which is to be measured, is prepared. The solution is left for 15 hours at 20° C. and coagulated. A load is applied on the surface of the thus obtained gel, and a maximum weight of the load, which the gel can withstand for 20 seconds, is measured. The value of the maximum weight per 1 $cm^2$ is called the gel strength of agar.

In contrast to the above-mentioned gel strength agar, there is a case where low gel strength of about 100 $g/cm^2$ is required. For example, such low gel strength is needed in agar used as a gelling agent for spread foods, cosmetics and soft-texture confectionery, or used as a fat replacer. In this case, in order to use normal agar, it is necessary to decrease the agar concentration, thereby lowering the gel strength. If the agar concentration is lowered to a certain level, however, water removal occurs and elasticity of texture is lost. In order to prevent such problems from arising, low gel strength agar is required, which has a low gel strength even if the agar concentration exceeds a certain level, and can produce a soft gel with no syneresis.

Figure 6A:
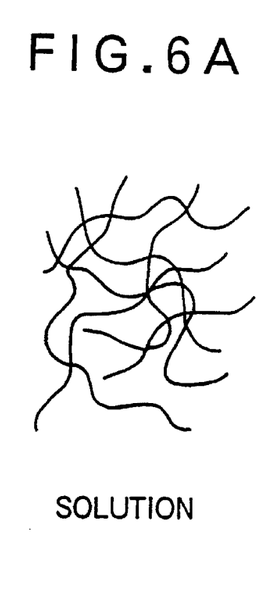
FIGS. 6A–6C are a view for explaining a gelation mechanism of agar.
Figure 6B:
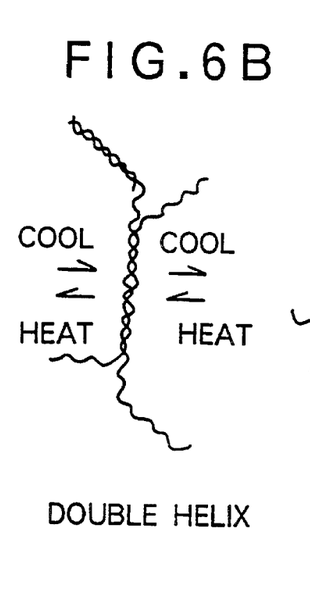
Figure 6C:
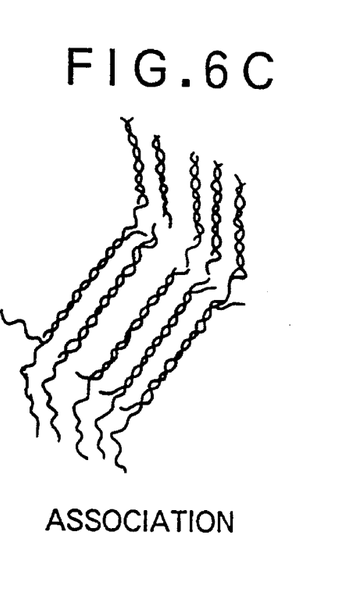

However, there is no conventional agar which can achieve a low gel strength of about 100 $g/cm^2$ when the agar concentration is 1.5%. One reason for this is that molecules of agar components (agarose and agaropectin) are long. Specifically, in a solution-state agar, molecules are present in a random coil state, as shown in FIG. 6A. When the solution-state agar is cooled, a three-dimensional network of a double helix structure is formed, as shown in FIG. 6B. Then, the sol state of the agar changes to the association state, as shown in FIG. 6C. Because of this gelation mechanism, the gel strength cannot be lowered if the molecules of agar are long.

Another reason for the high gel strength of conventional agar lies in the manufacturing process. In the prior art, seaweeds such as Gelidium and Gracilaria are used as raw material, and an agar solution is extracted. The agar solution is filtered and then cooled. Thus, the solution is once gelatinized. The obtained gel is pressurized and dehydrated, or the gel is frozen and thawed to separate a water component and then it is dehydrated. Thus, dried agar is obtained.

In the case of employing the pressurizing/thawing process, when an agar gel of a low gel strength is interposed between dehydrating cloths and pressurized, clogging occurs in the cloths and dehydration is not performed desirably. On the other hand, in the case of employing the freezing/denaturing process, an agar gel of a low gel strength does not have an orderly spongy structure, and it is caused to flow out with water. For these reasons, in the prior art, only agar with a predetermined gel strength or above can be obtained.

SUMMARY OF THE INVENTION

An object of the present invention is to provide low gel strength agar capable of producing a soft gel which has a low gel strength and is free from water removable, even when the agar concentration is increased to a certain level.

Another object of the invention is to provide a process of manufacturing such low gel strength agar with high efficiency.

Still another object of the invention is to provide foods with special properties not found in conventional foods, by using such low gel strength agar.

Still another object of the invention is to provide cosmetics with special effects not found in conventional cosmetics in which a thickener (a agent for increasing viscosity) is used, by using such low gel strength agar.

According to low gel strength agar of the present invention, the molecules of the agar are cut to short fragments, and the gel strength is adjusted to be 250 $g/cm^2$ or below at 1.5% agar concentration. Therefore, even when the agar concentration is increased to a certain level, a soft gel which has a low gel strength and is free from syneresis can be obtained.

According to a process of the invention of manufacturing low gel strength agar, the molecules of an agar constituent are cut by acid treatment, and the effect of an acid used in the acid treatment is eliminated by neutralization treatment. The acid treatment can be performed on dried agar pulverized in the process of manufacturing the agar. Alternatively, when agar subjected to a dehydration step after a coagulating step in the agar manufacturing process, or agar subjected to a freezing step and a thawing step in the agar manufacturing process, is re-dissolved without drying, the re-dissolved agar may be subjected to acid treatment. Further, the acid treatment may be performed at the time of an extraction step in the agar manufacturing process, or agar subjected to either state after an extraction step or a filtering step in the agar manufacturing process may be subjected to the acid treatment.

According to the process of the invention of manufacturing low gel strength agar, such low gel strength agar can be manufactured with high efficiency, and the gel strength of the manufactured agar does not decrease excessively.

The foods of the invention contains the above-mentioned low gel strength agar. The low gel strength agar, whose gel strength is adjusted to be 250 $g/cm^2$ or below at 1.5% agar concentration, is excellent in A) low calorie property, B) shape-retaining property, C) water retention property, D) improvement of texture, E) dietary fibers, F) thickening property, G) emulsification property, H) spinnability prevention, I) spreading property, and J) aging prevention property.

From these properties, foods with the following advantages can be obtained: 1) good flavor release of agar with no stickiness, 2) soft texture, 3) good shape-retaining property, 4) rich dietary fibers, 5) low calorie achieved by the water retention, 6) non-melt at normal temperatures by virtue of a high melting point, and 7) high safety achieved by natural food material.

The cosmetics of the present invention contain the above-mentioned low gel strength agar. The low gel strength agar, whose gel strength is adjusted to be 250 g/cm$^2$ or below at 1.5% agar concentration, has excellent fluidity even when it is used at high concentration. Thus, the cosmetics containing a large quantity of the low gel strength agar include much natural minerals, give the skin with moisture, and smooth and clean the skin. The reason for this is that the low gel strength agar is excellent not only in thickening properties but also in permeability. In addition, if the agar is applied to emulsified products such as milky lotion, the emulsification stability is enhanced.

DETAILED DESCRIPTION OF THE PREFERRED EMBODIMENTS

Embodiments of the present invention will now be described with reference to the accompanying drawings.

Figure 5:
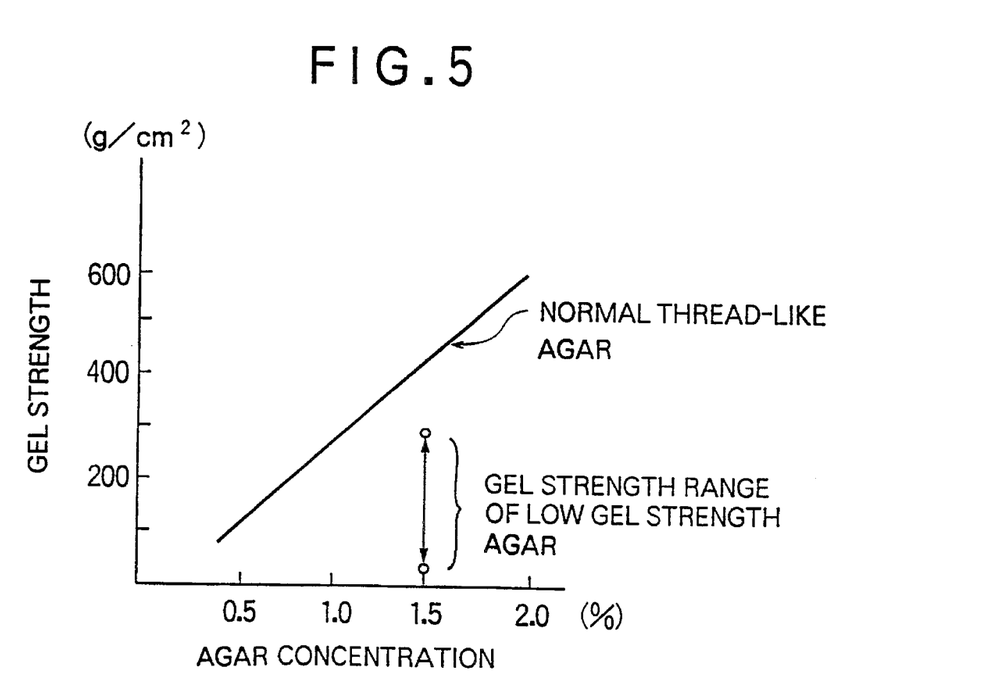
FIG. 5 is a characteristic graph showing the relationship between the agar concentration and gel strength.

The gel strength of low gel strength agar according to the present invention is limited, as shown in FIG. 5, to 250 g/cm$^2$ or less, and preferably in a range between 10 to 250 g/cm$^2$, at 1.5% agar concentration. The reason for this is that if the gel strength is less than 10 g/cm$^2$ at 1.5% agar concentration, a problem of syneresis arises, and if the gel strength exceeds 250 g/cm$^2$ at 1.5% agar concentration, the same problems as in normal or conventional agar arise.

The gel strength of 100 g/cm$^2$ or below cannot be measured by the above-described measuring method. In fact, by making use of the proportional relationship between the gel strength and agar concentration, the gel strength of 10 g/cm$^2$ at 1.5% agar concentration, for example, is measured as 100 g/cm$^2$ at 15% agar concentration.

It is not easy to quantitatively confirm the cutting of agar molecules for decreasing the gel strength in a range of 10 to 250 g/cm$^2$ at 1.5% agar concentration, nor is it necessary to do so. The simplest confirmation method is to collect data showing the relationship between the gel strength of agar, whose molecules were cut by acid or special enzyme, and the amount of added acid or enzyme. Thereby, reproducibility is obtained.

The special enzyme include α-agarase and β-agarase from *Pseudomonas atlantica*, Pseudomonas sp. and Luminous Bacterium, etc.

And a process for cutting the molecules of agar with the enzyme is as follows. β-agarase (30 units/1 g agar) is added to agar solution dissolved in phosphate buffer, and incubate 6 hours at 40° C. Then, the low gel strength agar is obtained by degradation of agar molecules.

Figure 4:
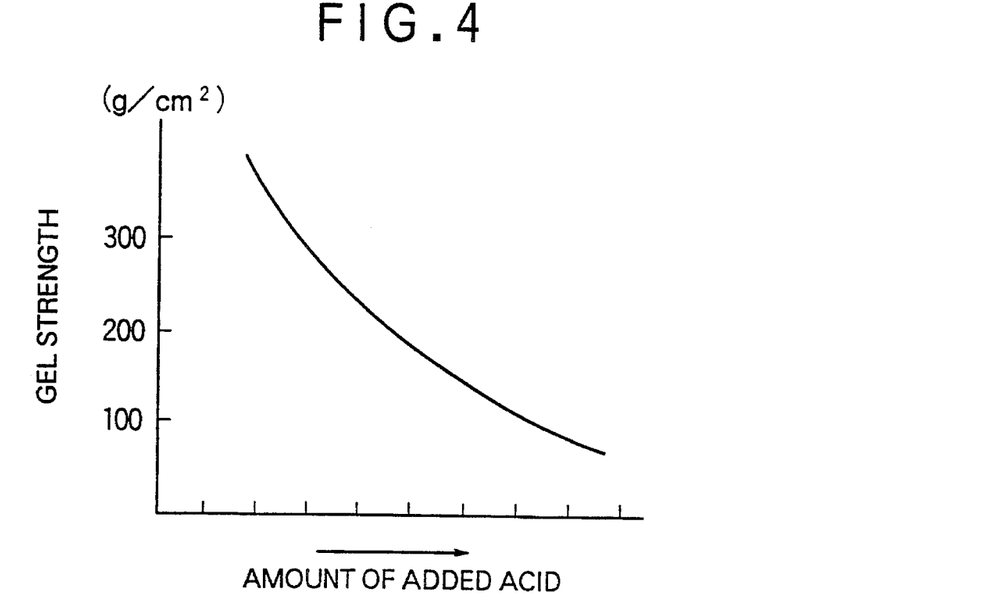
FIG. 4 is a characteristic graph showing the relationship between the amount of added acid and gel strength.

FIG. 4 shows a characteristic curve showing the relationship between the amount of added acid and the Gel strength (at 1.5% agar concentration). As seen from FIG. 4, the Gel strength (at 1.5% agar concentration) decreases in accordance with an increase in amount of added acid.

Example 1

0.5 part of sulfuric acid was added to 100 parts of agar. The resultant was heated at 70° C. for six hours, and it was neutralized by using caustic soda. As a result, low gel strength agar having a low gel strength of 200 g/cm$^2$ at 1.5% agar concentration was obtained.

Example 2

Two parts of acetic acid was added to 100 parts of agar. The resultant was heated at 85° C. for eight hours, and it was neutralized by using sodium carbonate. As a result, low gel strength agar having a low gel strength of 60 g/cm$^2$ at 1.5% agar concentration was obtained.

Example 3

Three parts of citric acid was added to 100 parts of agar. The resultant was heated at 80° C. for eight hours, and it was neutralized by using tribasic potassium phosphate. As a result, low gel strength agar having a low gel strength of 250 g/cm$^2$ at 1.5% agar concentration was obtained.

Since the agar of the present invention has a low gel strength, a soft gel free from water removal can be obtained. Thus, the low gel strength agar can suitably be used as a gelling agent for spread foods, cosmetics and soft-texture confectionery, or used as a fat replacer. The gel obtained by using such low gel strength agar has a behavior acting on thixotropy as thickening agent, rather than gel, and it can have a special shape-retaining property not found in other gelling agents. From these properties, the agar of this invention is applicable to the following:

| Applied Example 1: | honey spread | |
|---|---|---|
| | low gel strength agar | 2 parts |
| | honey | 78 parts |
| | water | 20 parts |
| Applied Example 2: | mayonnaise dressing with | |
| | low calorie | |
| | low gel strength agar | 5 parts |
| | yolk | 8 parts |
| | vinegar | 8 parts |
| | salad oil | 5 parts |
| | sugar | 6 parts |
| | salt | 2 parts |
| | spice | 0.2 part |
| | water | 65.8 parts |
| Applied Example 3: | soft adzuki-bean jelly | |
| | low gel strength agar | 1 part |
| | granulated sugar | 10 parts |
| | adzuki-bean and | |
| | thick syrup | 48 parts |
| | water | 41 parts |

The honey spread according to Applied Example 1 was experimentally produced, with the result that margarine-type honey spread with no spinnability was obtained.

Figure 1:
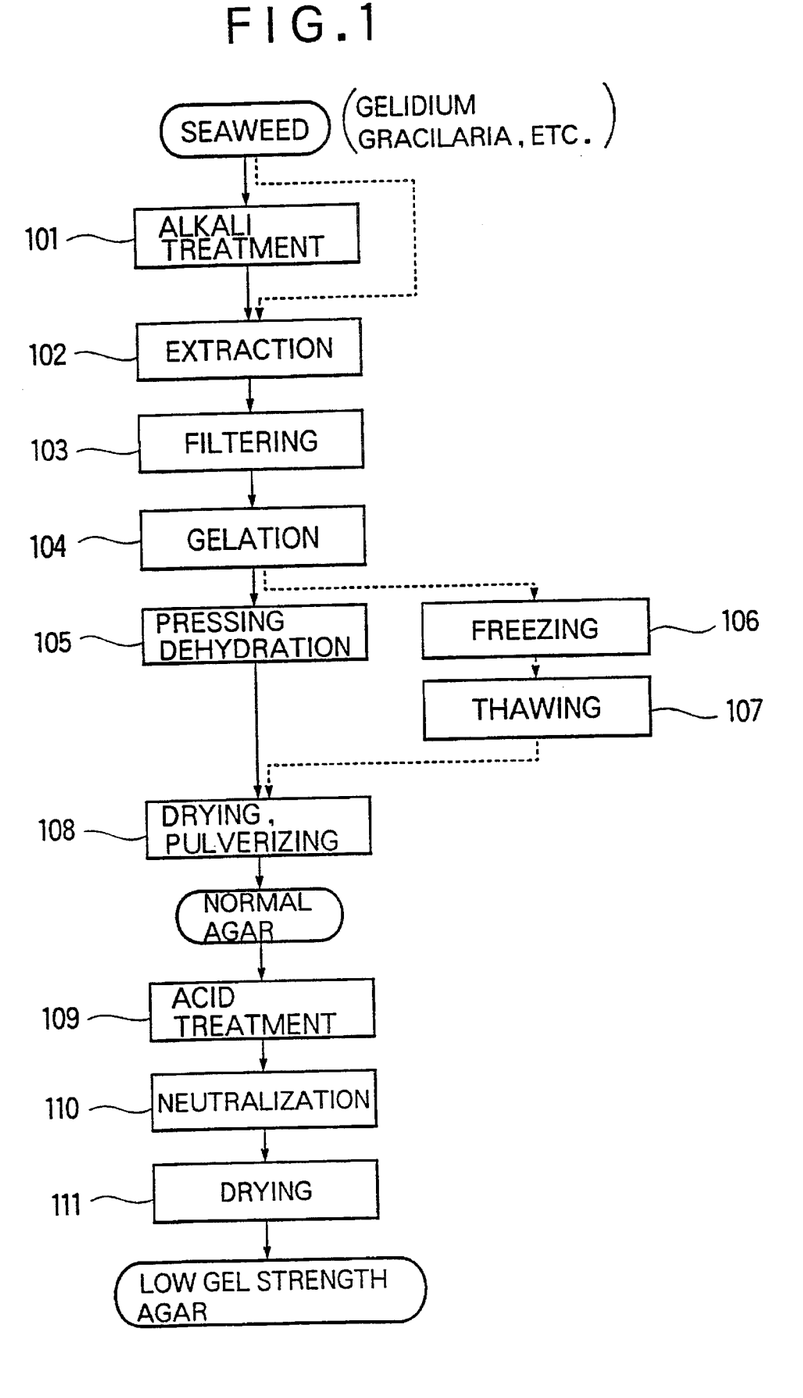
FIG. 1 shows steps of an example of a manufacturing process of the present invention.

Examples of the process of the present invention will now be described. FIG. 1 shows the steps of a first example of the process according to the invention. In step 101, seaweed such as Gelidium and Gracilaria, serving as raw material of agar, is subjected to alkali treatment to increase coagulation properties. If the alkali treatment is not necessary, this step 101 may be omitted, as indicated by a broken line. In step 102, extraction treatment is performed, and a solution containing agar component extracted from the seaweed. In step 103, the extracted solution is filtered, and in step 104 the filtered solution is coagulated (cooled). After step 104, the solution is gelatinized. Then, pressing dehydration is carried out in step 105, or dehydration by freeze-thawing is performed in freezing step 106 and melting step 107. Thus, the dehydrated agar material is dried and pulverized in step 108, and agar (in the pulverized state in this case) having a normal gel strength is obtained. Thus far, these steps are identical to conventional ones.

The constituents of the agar are polysaccharide having a basic skeleton of galactose and are classified into neutral agarose having good gelation properties, and ionic agar-opectin having no gelation properties. The structure of agarobiose, which is a repetition unit of agarose, consists of β-D-galactopyronose bonded at 1- and 3-positions, and 3,6-anhydro-α-L-galactopyranose bonded at 1- and 4-positions.

It is understood that agaropectin includes all ionic polysaccharide, other than agarose, in the agar. The agar-opectin has the same bonding structure as the agarose, but the former partly includes large amounts of sulfuric acid ester, methoxyl group, pyruvic acid group, and carboxyl group.

In this example, the pulverized agar obtained in step 108 is subjected to acid treatment in step 109, and the agar molecules are cut to decrease the gel strength to a desired value. Specifically, while a solution of prescribed acid (sulfuric acid, acetic acid, phosphoric acid, adipic acid, G.D.L., citric acid, malic acid, lactic acid, fumaric acid, gluconic acid, phytic acid, etc.) is sprayed on agar, the agar is uniformized in a blending machine. Thereafter, the agar is heated at 40 to 120° C. and subjected to hydrolysis for a predetermined time period.

Subsequently, neutralization is effected in step 110, and the acid used in step 109 is neutralized. Specifically, the acid is neutralized by spraying a solution of an alkali or alkaline salt (caustic soda, caustic potash, sodium carbonate, 4-sodium pyrophosphoric acid, 4-potassium pyrophosphate, sodium hydrogencarbonate, 3-potassium phosphate, 3-sodium phosphate, etc.) on the agar. Further, the agar is heated to recover water.

The agar subjected to the acid treatment and neutralization treatment in this manner is dried in step 111. Then, a low gel strength agar is obtained. For example, sulfuric acid was used and agar was heated at 80° C. for six hours, and thus a low gel strength agar having a gel strength of 100 g/cm² at 1.5% agar concentration was obtained.

According to the process of this example, normal dried agar product can be used in step 109, and a large quantity of low gel strength agar can be obtained at a time. In addition, energy cost is low. Furthermore, since the gel strength of agar can easily be controlled only by adjusting the amount of acid used in step 109, this process is suitable for industrialization.

Figure 2:
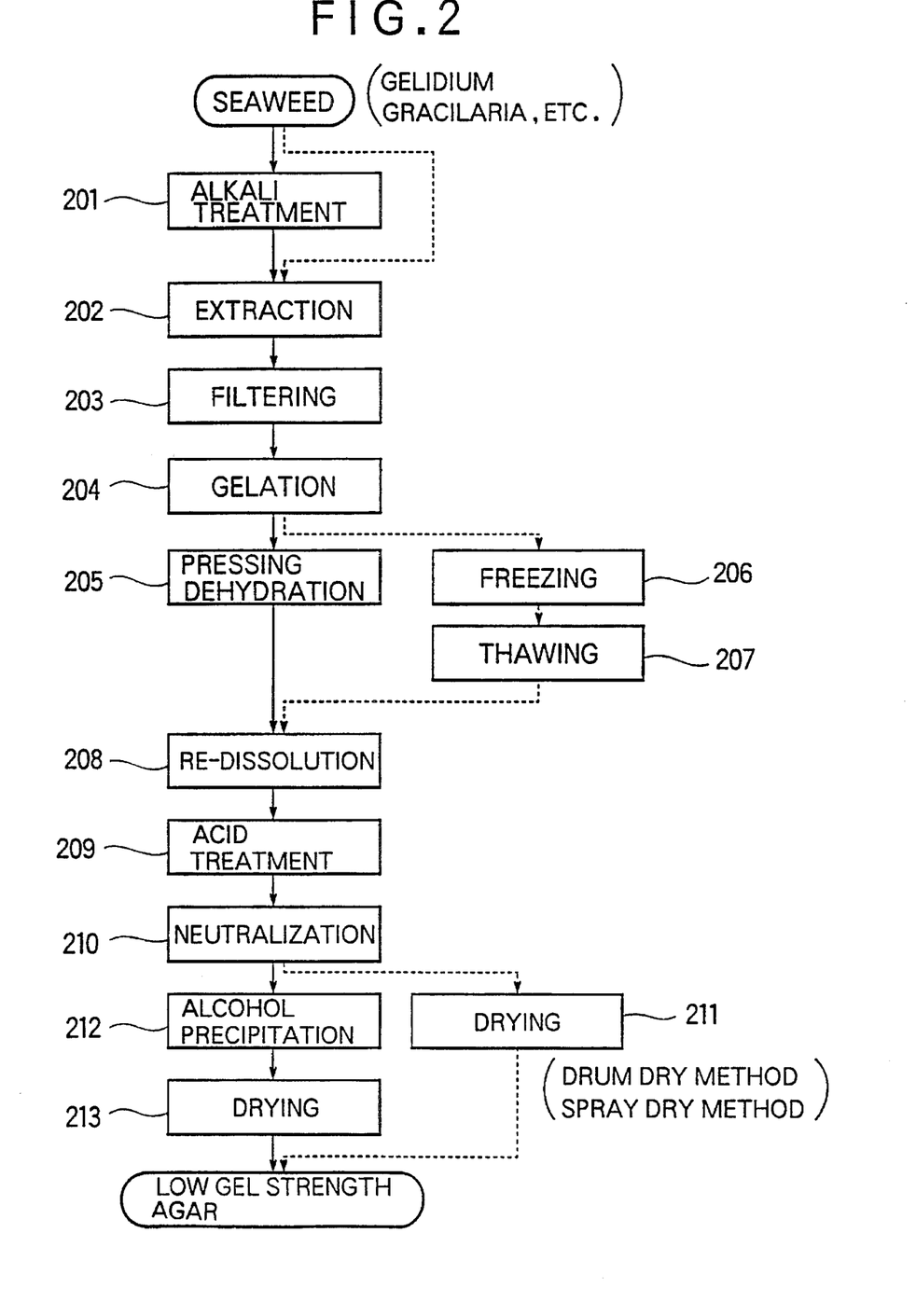
FIG. 2 shows steps of another example of the manufacturing process of the invention.

FIG. 2 shows the steps of a second example of the process according to the invention. In step 201, seaweed such as Gelidium and Gracilaria, serving as raw material of agar, is subjected to alkali treatment to increase gelation properties. If the alkali treatment is not necessary, this step 201 may be omitted, as indicated by a broken line. In step 202, extraction treatment is performed, and a solution containing agar component is extracted from the seaweed. In step 203, the extracted solution is filtered, and in step 204 the filtered solution is solidified (cooled). After step 204, the solution is gelatinized. Then, pressing dehydration is carried out in step 205, or dehydration by freeze-thawing is performed in freezing step 206 and thawing step 207.

These steps are the same as shown in FIG. 1. In the second example, the dehydrated agar gel is not dried, but it is re-dissolved in step 208, or dried agar is re-dissolved in step 208. Acid is applied to the re-dissolved liquid-phase agar in step 209, and the resultant agar is heated and decomposed. In this case, if the liquid-phase agar is a diluted solution, it is difficult to perform drying in step 211 or recovery in alcohol precipitation step 212. Thus, the agar concentration is set at a high value. For this reason, the re-dissolving in step 208 is effected under pressure.

In step 210, neutralization treatment is performed after acid treatment in step 209, like step 110 in FIG. 1. After step 210, drying treatment is performed in step 211 by a drum dry method or a spray dry method, thereby obtaining low gel strength agar. Alternatively, alcohol precipitation is effected in step 212 after step 210, and drying treatment is performed in step 213, thereby obtaining low gel strength agar.

According to the manufacturing process of this example, by raising the heating temperature at the re-dissolving in step 208, the amount of acid used in step 209 can be reduced. Further, the drum dry method can be used in step 211, the low gel strength agar being powdered and easy to dissolve can be manufactured.

Figure 3:
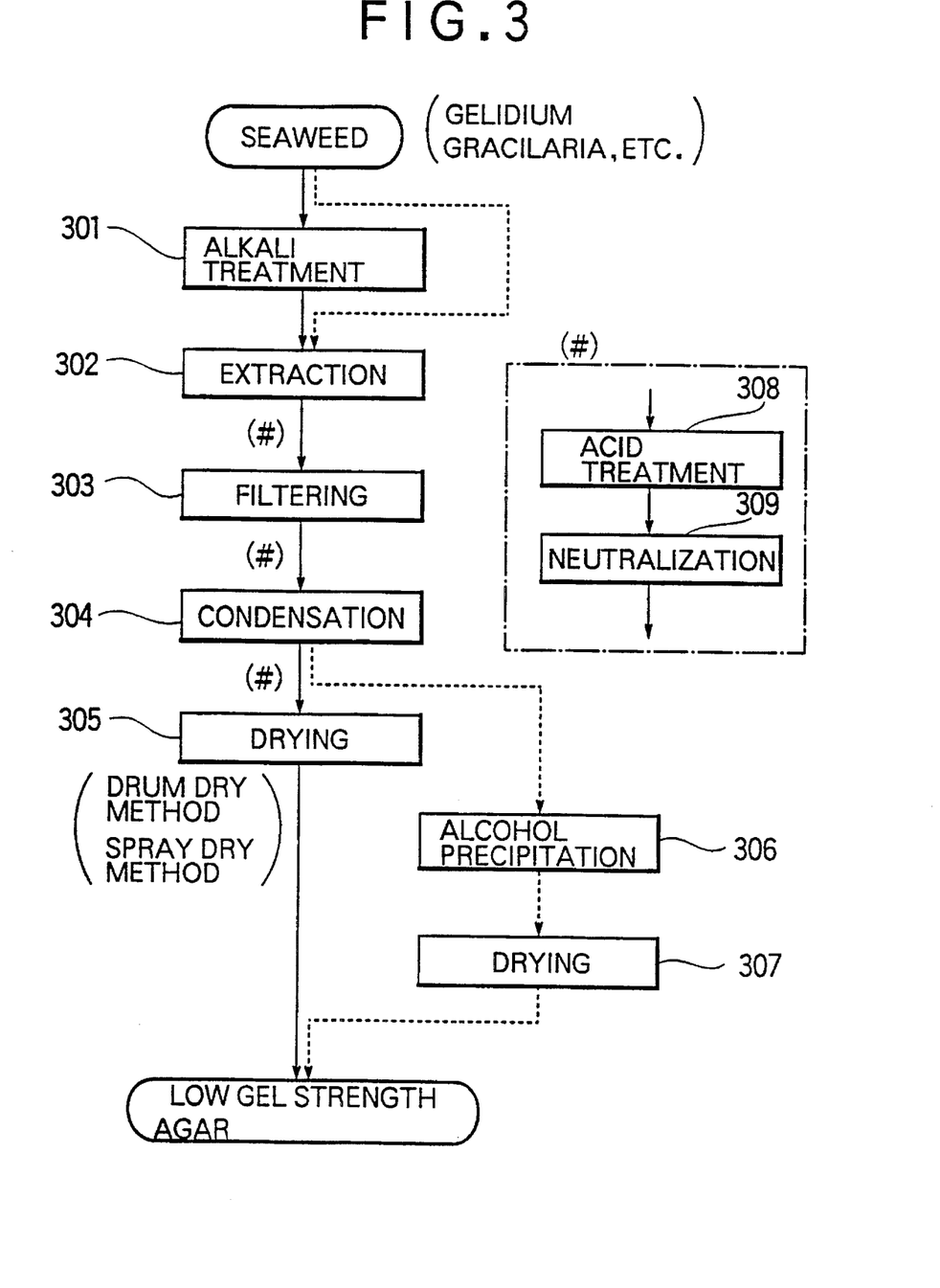
FIG. 3 shows steps of still another example of the manufacturing process of the invention.

FIG. 3 shows the steps of a third example of the process according to the invention. In step 301, seaweed such as Gelidium and Gracilaria, serving as raw material of agar, is subjected to alkali treatment to increase gelation properties. If the alkali treatment is not necessary, this step 301 may be omitted, as indicated by a broken line. In step 302, extraction treatment is performed, and a solution containing agar component is extracted from the seaweed. In step 303, the extracted solution is filtered, and in step 304 the filtered solution is condensed. Then, the condensed solution is dried in step 305 by a drum dry method or a spray dry method, or alcohol precipitation is effected in step 306 and drying treatment is performed in step 307, thereby obtaining low gel strength agar.

In this case, in order to lower the gel strength of the finished agar, an acid treatment step 308 and a neutralization step 309 are performed at the time of extraction step 302 or after extraction step 302 or filtering step 303 (indicated by mark #). If acid treatment step 308 and neutralization step 309 are performed at the time of extraction step 302 or just after extraction step 302, the subsequent steps become easier.

According to this manufacturing process, unlike the processes of FIGS. 1 and 2, the condensation step 304 is required. In addition, when drying treatment is performed directly in step 305, without alcohol precipitation as in step 306, the finished low gel strength agar becomes crude agar.

According to the above-described low gel strength agar of this invention, there can be obtained a soft gel which is free from water removable and has a low gel strength even at a certain concentration level or above. The agar is high-stability and high-safety food, and is rich in dietary fibers. In addition, as compared to other thickening agents, the agar has good flavor release and less stickiness. Furthermore, according to the process of the invention of manufacturing agar, such low gel strength agar can be manufactured with high efficiency.

The gel obtained by using such low gel strength agar has a behavior acting on thixotropy as thickening agent, rather than gel, and it can have a special shape-retaining property not found in other gelling agents.

Table 1 (below) shows the relationship between foods containing the low gel strength agar of this invention and the above-mentioned advantages A to J. Most expectable advantages are indicated by a mark #, and normally expectable advantages are by a mark +.

TABLE 1

| Foods | advantages | | | | | | | | | |
|---|---|---|---|---|---|---|---|---|---|---|
| | A | B | C | D | E | F | G | H | I | J |
| Butter | # | + | + | + | + | − | + | − | + | − |
| Margarine | # | + | + | + | + | − | + | − | + | − |
| Chocolate/peanut cream | # | + | + | + | + | − | + | − | + | − |
| Ice cream | # | + | + | + | + | + | + | − | − | − |
| Sherbet | − | + | + | # | + | − | + | − | − | − |
| Shake | # | + | + | + | + | + | + | − | − | − |
| Mayonnaise | # | + | + | + | + | + | + | − | − | − |
| Dressing | # | + | + | + | + | + | + | − | − | − |
| Cheese food | # | + | + | + | + | − | − | − | + | − |
| Yogurt | + | + | + | # | + | − | − | − | − | − |
| Pudding, jelly | + | + | + | # | + | − | − | − | − | − |
| Milk shake | # | − | + | + | + | + | + | − | − | − |
| Mousse, whipping cream | # | + | + | + | + | + | + | − | − | − |
| Meat products such as hamburg steak and ham | # | + | + | + | + | − | − | − | − | − |
| Sauce, ketchup | + | + | + | # | + | − | − | − | − | − |
| Japanese sauces | − | + | + | # | + | + | − | + | − | + |
| Jam, honey, condensed milk | − | + | + | # | + | + | − | # | + | − |
| Beverages (juice) | − | − | − | + | # | + | − | − | − | − |
| Confectionery (caramel, chewing gum) | + | + | + | # | + | − | − | + | − | − |
| Noodles (Chinese noodle, "soba" noodle, "udon" noodle) | + | − | + | # | + | − | − | − | − | + |
| Japanese confectionery (soft adzuki-bean jelly, "kingyoku") | − | + | + | # | + | − | − | − | − | # |
| Japanese confectionery (rice cakes, a bean-jam bun) | − | − | − | + | + | − | − | − | − | # |
| Bread | + | − | + | # | + | − | − | − | − | + |
| Icing | − | # | + | + | + | + | + | − | + | − |
| Fish-paste product | + | + | + | # | + | − | − | − | − | − |
| Rice | − | − | − | # | − | − | − | − | − | + |

On the basis of the most expectable advantages, the above foods containing the low gel strength agar may roughly be classified into (1) dietary fibers drinks, (2) low-calorie foods, (3) texture-improved foods, and (4) aging-prevention foods.

Foods in group (1) are beverages enriched with dietary fibers by use of low gel strength agar. Foods in group (2) have low fats and oils and low calorie, since fat and oil constituents thereof are replaced by aqueous low gel strength agar spread components. Foods in group (3) have improved texture such as good flavor release. Foods in group (4) aim at preventing aging of starch, etc.

The foods according to the present invention will now be described in greater detail. Low gel strength agar, whose molecules were cut to short fragments and whose gel strength was adjusted to 250 $g/cm^2$ or below at 1.5% agar concentration, is contained in low-calorie foods. The low-calorie foods include spreads (butter, margarine, chocolate cream, peanut butter etc.), ice products (ice cream, ice sherbet, shake, etc.), seasonings (mayonnaise, dressing, etc.), dairy products (cheese food, yogurt, pudding, milk shake, mousse, whipping cream, etc.), and meat products (hamburg steak, ham, etc.). In a wider sense, the low-calorie foods include low-calorie pet foods.

Recently, much attention has been paid to diseases of adult people such as obesity, cancer and heart disease, due to excessive caloric intake. Thus, various low-calorie foods using a system with less or no fats and oils are commercially available. However, if the calorie in foods is decreased, the flavor, taste, texture and shape-retention properties of such foods are generally degraded compared with original foods containing usual fats and oils.

The reason for this is that in order to achieve a low fat-and-oil and low calorie system in the prior art, stabilizers such as starch, gelatin and gum is added, and/or constituents are controlled by adding protein or an emulsifying agent. That is, if a food is produced with a starch or gelatin system to maintain shape-retaining properties and water-retention properties, stickiness is caused in the food. And the food is not easily melted owing to reduction of fats and oils. In addition, since flavor is lost due to starch, flavor release is degraded.

The salient feature of agar is a gelatinizing force. In particular, unlike other gelling agents water-removing properties are high despite the fact that a "crispy" texture gel can be obtained with high shape-retention properties. Thus, when the agar is applied to jelly-like foods, good flavor release as well as smooth texture can be achieved.

However, the texture of the food, of which calorie is to be lowered, is undesirably changed by the gelatinizing force of the normal agar. It is not possible to increase the use concentration of the normal agar (e.g. 0.5% or above). Thus, it is difficult to reflect the inherent properties of the prior-art agar on foods.

By contrast, these prior-art problems can be solved by the low-calorie foods according to the present invention, which contain the low gel strength agar whose gel strength is adjusted to 250 $g/cm^2$ or below at 1.5% agar concentration. The reason for this is that the low gel strength agar has shape-retention properties and extension properties, and that the flavor of the original food can be reproduced by virtue of the flavor release of the low gel strength agar even if the fats and oils are reduced.

In addition, since the foods according to the present invention contain the low gel strength agar, the foods can have improved texture not found in prior art foods. For example, foods gelatinized by agar can be softened, which include jelly products (milk jelly, fruit jelly, etc.), hard-type yogurt consisting mainly of yogurt, and Japanese confectionery (soft adzuki-bean jelly, "kingyoku", etc.).

Table 2 shows the relationship between the use concentration of agar, gel strength, and water-removal amount.

TABLE 2

| | Gel Strength at 1.5% Concentration | Use Concentration |
|---|---|---|
| Normal agar | 600 g/cm$^2$ | 0.30% |
| Low gel strength agar 1 | 200 g/cm$^2$ | 0.85% |
| Low gel strength agar 2 | 100 g/cm$^2$ | 1.60% |

| | Gel Strength of Produced jelly | Syneresis Amount |
|---|---|---|
| Normal agar | 120 g/cm$^2$ | 1700 mg |
| Low gel strength agar 1 | 120 g/cm$^2$ | 800 mg |
| Low gel strength agar 2 | 130 g/cm$^2$ | 550 mg |

As is clear from Table 2, the lower the gel strength of agar, the less the syneresis amount.

Thus, the following advantages can be expected:

1) Foods with a low syneresis amount can be achieved while a soft texture is maintained.

2) A special elasticity of food can be achieved by using the low gel strength agar at a certain concentration or above. For example, by adding low gel strength agar of 30 g/cm$^2$ to milk, the same texture as a yogurt-like curd can be achieved.

3) Hard-type yogurt has special texture by virtue of functions of gelatin and agar. The same texture can be achieved without gelatin, if the low gel strength agar is used. The solidity of conventional yogurt in which gelatin is used may vary due to a variation in temperature, since the melting point of gelatin is low. Such a problem does not arise in yogurt in which the low gel strength agar is used.

4) If the low gel strength agar is applied to soft adzuki-bean jelly, the jelly can be softened, and the settling of adzuki-bean jam can be prevented since the use concentration of the low gel strength agar can be increased.

Examples of foods according to the present invention will now be described.

Low-calorie margarine according to this invention contains the low gel strength agar, whose gel strength is adjusted to 250 g/cm$^2$ or below at 1.5% agar concentration, as a fat replacer. For example, it has the following composition:

Example 4: Low-calorie margarine

| (Constituents) | (Product of the Invention) |
|---|---|
| fats and oils | 25.0 parts |
| saccharides | 15.0 parts |
| emulsifying agent | 3.0 parts |
| salt | 0.6 part |
| spice | 1.5 parts |
| color (carotene) | 0.2 part |
| low gel strength agar | 2.0 parts |
| water | 52.7 parts |

According to a conventional method of decreasing the calorie of margarine, thickener such as gelatin or lactic components are added. If this method is used, however, stickiness is inevitably caused.

On the other hand, if agar is used, crispy texture with good flavor release can be achieved, and therefore the special flavor of margarine can be maintained. Conventional agar has the same flavor release, but its gelatinizing force is stronger, and if the agar concentration is higher than a certain level (e.g. 0.4% or above), the texture becomes rough. If the margarine is quickly pulverized to fine particles by a homomixer for obtaining a soft spread, the shape-retention properties of the soft spread are degraded, and the texture of conventional margarine cannot be achieved. In addition, if the agar concentration is increased, the texture becomes rough. By contrast, if the low gel strength agar is used in margarine, like the present invention, the texture does not become rough.

Dressing according to this invention contains the low gel strength agar whose gel strength is adjusted to 250 g/cm$^2$ or below at 1.5% agar concentration. For example, it has the following composition:

Example 5: French dressing

| (Constituents) | (Prior-art Product) | (Product of the Invention) |
|---|---|---|
| water | 35.0 parts | 62.0 parts |
| vegetable fats and oils | 40.0 parts | 10.0 parts |
| sugar | 11.0 parts | 10.0 parts |
| vinegar | 10.0 parts | 13.3 parts |
| salt | 1.0 part | 1.0 part |
| spice | 2.0 parts | 2.0 parts |
| perfume | 0.1 part | 0.1 part |
| seasoning | 0.5 part | 0.4 part |
| xanthane gum | 0.3 part | 0.1 part |
| guar gum | 0.1 part | — |
| low gel strength agar | — | 1.0 part |
| locust been gum | — | 0.2 part |

Conventionally, in French dressing, Russian dressing, emulsified Italian dressing, etc., a stabilizer such as xanthane gum or guar gum is used for stabilizing emulsification between water, vinegar and vegetable fats. Since there has recently been a demand for lowering the calorie of dressing, an thickener such as carrageenan, pectin, locust been gum is added to create substitute texture for fats in addition to the stabilizer.

However, with such low-calorie dressing, texture with fatty-bead cannot be obtained, and stickiness by the thickener occurs. In addition, the taste of fats is hidden, and so the taste of dressing is more degraded than is supposed by the reduction in fats.

In this case, however, the French dressing of the present invention has good flavor release of the low gel strength agar, which creates more flavor with low fats.

Cheese spreads or cheese foods according to this invention contains the low gel strength agar, whose gel strength is adjusted to 250 g/cm$^2$ or below at 1.5% agar concentration, as a substitute for natural cheese. For example, it has the following composition:

Example 6: Cheese spreads/cheese foods

| (Constituents) | (Prior-art Product) | (Product of the Invention) |
|---|---|---|
| natural cheese | 70.0 parts | 18.0 parts |
| salt | 0.2 part | 0.8 part |
| color (carotene) | 0.1 part | 0.2 part |
| skim milk powder | 4.0 parts | 15.0 parts |
| cream | 8.0 parts | — |
| powder whey | 7.0 parts | 14.0 parts |
| emulsifying agent | 0.1 part | 0.2 part |
| cheese perfume | 0.5 part | 1.2 part |
| water | 10.0 parts | 48.3 parts |

-continued

| Example 6: Cheese spreads/cheese foods | | |
|---|---|---|
| (Constituents) | (Prior-art Product) | (Product of the Invention) |
| low gel strength agar | — | 2.3 part |

Normal natural cheese contains about 30% of fats. Thus, a conventional cheese spread using much normal natural cheese also contains about 25% of fats.

By contrast, in the product of the invention using the low gel strength agar, the cheese content can be reduced without adversely affecting the texture. Thus, a cheese spread or cheese food with less fats can be achieved.

Conventional products using much cheese have peculiar stickiness and are not easily melted in the mouth. The spread of this invention using low gel strength agar with less cheese has little stickiness and is easily melted in the mouth, with good flavor release.

Some kind of matters such as pickles or dry fruits may be added to cheese spreads or cheese foods. In the conventional spreads, it cannot be said that the taste of added matters is fully enjoyed. By contrast, if the low gel strength agar is added, as in the product of the present invention, the taste of added matters can be fully enjoyed, and a range of selections of seasoning and flavoring can be widened.

Terrine according to this invention contains the low gel strength agar whose gel strength is adjusted 250 g/cm$^2$ or below. For example, it has the following composition:

| Example 6B: Terrine | |
|---|---|
| (Constituents) | |
| low gel strength agar | 1 part |
| tuna paste | 20 parts |
| salmon paste | 20 parts |
| ketchup | 12 parts |
| mayonnaise | optimum |
| shrimp | optimum |
| lemon juice | 3 parts |
| water | 24 parts |

Comparing to prior-art gelatine terrine, the terrine obtained by this invention has soft texture, shape-retention properties with high temperature.

A hamburg steak according to this invention contains the low gel strength agar whose gel strength is adjusted to 250 g/cm$^2$ or below at 1.5% agar concentration. For example, it has the following composition:

| Example 7: Hamburg | | |
|---|---|---|
| (Constituents) | (Prior-art Product) | (Product of the Invention) |
| lean meat | 99.0 parts | 89.0 parts |
| water | — | 9.6 parts |
| salt | 0.4 part | 0.4 part |
| perfume | 0.1 part | 0.1 part |
| spice | 0.5 part | 0.5 part |
| low gel strength agar | — | 0.4 part |

Conventional low-fat hamburg steaks, in most cases, use carrageenan. If carrageenan is used for reducing the calorie of a hamburg steak, the texture of the hamburg steak differs from that of ordinary hamburg steaks and a person who eats it feels a sense of such a difference.

By contrast, if the low gel strength agar is used, as in the present invention, a texture similar to that of a normal hamburg steak can be obtained. Since the melting point of low gel strength agar is higher than that of carrageenan, the amount of agar to be melted is small and meat juice can be contained inside the hamburg steak, when the hamburg steak is heated.

The same technique is applicable to other processed meat products such as ham, wiener, corned beef and meat loaf, and to secondary products such as "gyoza" (a fried dumpling stuffed with minced pork), "shao-mai" and meat balls. In addition, this technique is also applicable to pet food, and meet a recent demand for low-calorie pet food.

Ice cream according to this invention contains the low gel strength agar whose gel strength is adjusted to 250 g/cm$^2$ or below at 1.5% agar concentration. For example, it has the following composition:

| Example 8: Ice cream | | | |
|---|---|---|---|
| (Constituents) | (Prior-art Product) | (Product 1 of the Invention) | (Product 2 of the invention) |
| raw cream | 13.00 parts | 13.00 parts | — |
| butter | 5.00 parts | 5.00 parts | — |
| whole milk powder | 20.00 parts | 20.00 parts | 7.00 parts |
| skim milk powder | 6.00 parts | 6.00 parts | 3.00 parts |
| powder thick malt syrup | 3.00 parts | 3.00 parts | 5.00 parts |
| sugar | 6.00 parts | 6.00 parts | 10.00 parts |
| carrageenan | 0.10 part | — | — |
| guar gum | 0.10 part | — | — |
| gelatin | 0.15 part | — | — |
| emulsifying agent | 0.15 part | 0.15 part | 0.15 part |
| perfume | 0.12 part | 0.12 part | 0.20 part |
| salt | 0.02 part | 0.02 part | 0.02 part |
| color (carotene) | 0.02 part | 0.02 part | 0.03 part |
| low gel strength agar | — | 1.00 part | 1.50 part |
| water | 48.00 parts | 48.00 parts | 73.00 parts |

Conventional ice cream prepared according to a common recipe contains various stabilizers (carrageenan, gums, gelatin) in order to solve problems such as over-run characteristics, melt-down resistance, whey separation, and sandy condition. It is very difficult to determine an optimal adding rate of stabilizers so as to compensate their respective characteristics each other. Therefore, a great deal of time and work is required in only determining the recipe. In manufacturing factories, too, the manufacturing process is complex owing to the delicate recipe.

By contrast, if low gel strength agar is used, as in the present invention, all characteristics required for ice cream can be satisfied, and the complex manufacturing process does not need to be performed.

Further, if the low gel strength agar is used, the melt-down resistance, among the characteristics required for ice cream, is remarkably improved, as compared to the case where other stabilizers are used. This is because the low gel strength agar has a higher melting point than other gelling agents and gums. The advantages obtained by adding the low gel strength agar to the ice cream are also obtainable with ice mix, lact-ice, and soft cream.

In general, in order to achieve good over-run characteristics, the necessity of aging increases as the total solid constituent decreases. If the low gel strength agar is used, as in the present invention, the aging effect can be enhanced and therefore the over-run characteristics can be improved.

According to the present invention, low-calorie ice cream of Product 2 of Example 8 can be manufactured. The reason for this is that, in addition to the above-mentioned characteristics of the low gel strength agar, a fine and soft gel structure of the low gel strength agar can achieve a texture very similar to the texture of ice cream created by agglomeration of milk fats. Thus, tasty and low-calorie ice cream can be produced.

Low-calorie mayonnaise according to this invention contains the low gel strength agar whose gel strength is adjusted to 250 g/cm$^2$ or below at 1.5% agar concentration. For example, it has the following composition:

| Example 9: Low-calorie mayonnaise | |
| --- | --- |
| (Constituents) | (Product of the Invention |
| low gel strength agar | 5.0 parts |
| yolk | 8.0 parts |
| vinegar | 8.0 parts |
| salad oil | 5.0 parts |
| sugar | 6.0 parts |
| salt | 2.0 parts |
| spice | 0.2 part |
| water | 65.8 parts |

If low gel strength agar is used in low-calorie mayonnaise, shape-retention properties can be maintained, despite the fact that a fatty constituent is decreased. In addition, a elastic and smooth texture can be obtained, with better flavor release than other thickener.

Milk shake according to this invention contains the low gel strength agar whose gel strength is adjusted to 250 g/cm$^2$ or below at 1.5% agar concentration. For example, it has the following composition:

| Example 10: Milk shake | | |
| --- | --- | --- |
| (Constituents) | (Prior-art Product) | (Product of the Invention) |
| skim milk powder | 10.00 parts | 10.00 parts |
| raw cream | 35.00 parts | 5.00 parts |
| sugar | 11.00 parts | 11.00 parts |
| powder bean | 4.00 parts | 4.00 parts |
| glyceric fatty ester | 0.04 part | 0.04 part |
| water | 40.00 parts | 60.00 parts |
| carrageenan | 0.03 part | — |
| low gel strength agar | — | 0.50 part |
| powder whey | — | 5.00 parts |
| perfume | 0.20 part | 0.40 part |

In prior-art products, raw cream or milk fat is used, and so the calorie per meal is very high. By contrast, the milk shake of the present invention using low gel strength agar has a low calorie and a suitably elastic texture.

If a gelling agent other than agar or starch is used, the obtained milk shake is not smoothly melted in the mouth and is hard to drink because of stickiness. However, if the low gel strength agar is used, such a problem does not arise. In addition, the low gel strength agar is an excellent supply source of dietary fibers, and therefore various dietary fiber drinks can be realized by using the agar singly or in combination with other vegetable fibers.

Frozen dessert (ice sherbet) according to this invention contains the low gel strength agar whose gel strength is adjusted to 250 g/cm$^2$ or below at 1.5% agar concentration. For example, it has the following composition:

| Example 11: Frozen dessert (ice sherbet) | | |
| --- | --- | --- |
| (Constituents) | (Prior-art Product) | (Product of the Invention) |
| sugar | 24.0 parts | 24.0 parts |
| grape sugar | 8.0 parts | 8.0 parts |
| skim milk powder | 5.0 parts | 5.0 parts |
| fruit juice | 5.0 parts | 5.0 parts |
| perfume | 0.3 part | 0.3 part |
| color | 0.1 part | 0.1 part |
| pectin | 0.2 part | — |
| polysaccharides (gums) | 0.2 part | 0.1 part |
| water | 50.0 parts | 50.0 parts |
| low gel strength agar | — | 0.6 part |

In general, stabilizers such as MC, CMC, carrageenan, pectin or vegetable gum are used in ice sherbet, in order to achieve suitable over-run characteristics and produce a smooth frazil ice structure. The prior-art sherbet using such stabilizers has a good structure, but remainder, stickiness and thirst is felt during or after eating, and it is not satisfactory.

By contrast, the product of this invention using the low gel strength agar, eliminating the prior-art sensuous defect, can be smoothly melted in the mouth with good flavor release. In addition, by virtue of the gelatinizing force and shape-retention properties of the low gel strength agar, the melt-down resistance of the product can be improved. Furthermore, since the use of low gel strength agar can enhance over-run characteristics of the product, the product can be provided with shortness. Thus, crunch-type ice sherbet can be produced.

Yogurt according to this invention contains the low gel strength agar, whose gel strength is adjusted to 250 g/cm$^2$ or below at 1.5% agar concentration, as a substitute for normal agar. For example, it has the following composition:

| Example 12: Yogurt | | | |
| --- | --- | --- | --- |
| (Constituents) | (Prior-art Product) | (Product 1 of the Invention) | (Product 2 of the Invention) |
| milk | 98.0 parts | 98.0 parts | 98.0 parts |
| granulated sugar | 10.0 parts | 10.0 parts | 10.0 parts |
| gelatin | 0.4 part | 0.3 part | — |
| conventional agar | 0.2 part | — | — |
| low gel strength agar | — | 0.3 part | 0.6 part |
| starter | 1.4 part | 1.4 part | 1.4 part |

In accordance with a recent trend of diversification of foods, there is a demand that hard-type yogurt, which is hardened by use of agar or gelatin, have a finer, more delicate texture.

Agar and gelatin have been used as shape-retention agents for determining the texture of hard-type yogurt, because the solidity of agar does not considerably vary in relation to a temperature change (between a freezing temperature and a normal temperature, e.g. 30° C. in the summer), the agar is not relatively hard at low concentration (0.4% or less) and flavor release is good, and the gelatin has good water-retention properties and a soft texture can be achieved.

However, a softer texture is not obtained with conventional agar or gelatin. For example, if a texture is to be created with only use of gelatin, while the use concentration of agar is lowered or agar is not used, the temperature control in the manufacturing process becomes difficult because of the time-basis change of strength of gelatin and the low melting point of gelatin. Furthermore, the texture of product yogurt is not stabilized.

By contrast, if the low gel strength agar is used as shape-retention agent, as in the Product 1 of Example 12, yogurt of a soft, creamy texture, which is free from the above problem, can be produced. A soft similar texture can be produced as a substitute for curd of yogurt. Thereby, the fatty constituent of yogurt can be reduced, and a dietary (low-calorie) yogurt can be obtained with the same texture as a conventional one.

Further, like Product 2 of Example 12, the gelatin of conventional yogurt can be replaced with low gel strength agar, and it is not necessary to add two kinds of gelling agents in the manufacturing process. Besides, since the low gel strength agar has a coagulation point lower than that of conventional agar by 5° to 10° C., the culture temperature at which the starter is added can be lowered. Thereby, lacto bacilli can function more effectively.

Soft adzuki-bean jelly according to this invention contains the low gel strength agar, whose gel strength is adjusted to 250 g/cm$^2$ or below at 1.5% agar concentration. For example, it has the following composition:

| Example 13: Soft adzuki-bean jelly | | | |
|---|---|---|---|
| (Constituents) | (Prior-art Product) | (Product 1 of the Invention) | (Product 2 of the Invention) |
| sugar | 40.00 parts | 40.00 parts | 40.00 parts |
| adzuki-bean jam | 32.00 parts | 32.00 parts | 32.00 parts |
| conventional agar | 0.35 part | 0.20 part | — |
| low gel strength agar | — | 0.30 part | 0.60 part |
| arrowroot starch | 0.30 part | — | — |

If the low gel strength agar is contained in soft adzuki-bean jelly, as in the product of the invention, precipitation of bean jam can be prevented. When a conventional soft adzuki-bean jelly of the prior-art product is subjected to secondary sterilization (retort sterilization, boil sterilization), bean jam is precipitated and separated. As a result, a transparent jelly layer is formed. Thus, in the prior art, a thickener such as arrowroot starch, carrageenan, tamarind, or locust is added for thickening, thereby preventing precipitation of bean jam. However, if such an additive is used, stickiness occurs and the flavor of bean jam is lost. Further, since the arrowroot starch ages with the passing of time, the texture of jelly changes.

By contrast, if the low gel strength agar is used singly, as in the Product 2 of Example 13, or in combination with conventional agar, as in the Product 1 of Example 13, the bean jam does not precipitate and a soft adzuki-bean jelly having good flavor release, which cannot be found in conventional products, can be obtained.

A Japanese confectionery so called "Kingyoku" according to this invention contains the low gel strength agar whose gel strength is adjusted to 250 g/cm$^2$ or below at 1.5% agar concentration. For example, soft grape jelly has the following composition:

| Example 14: Soft grape jelly | |
|---|---|
| (Constituents) | (Product of the Invention) |
| low gel strength agar | 2 parts |
| sugar | 560 parts |
| thick malt syrup | 170 parts |
| wild vine juice | 340 parts |
| water (including evaporation amount) | 200 parts |

In the prior art, in order to produce soft jelly with low gel strength, it is necessary to decrease the use concentration of agar. However, if the use concentration of conventional agar is lowered, water-removal amount increases. Thus, the produced jelly has a problem as goods to be sold.

By contrast, if the low gel strength agar is used, as in the present invention, water removal does not occur even if the use concentration is low, and therefore novel soft jelly can be obtained.

Gummy jelly according to this invention contains the low gel strength agar, whose gel strength is adjusted to 250 g/cm$^2$ or below at 1.5% agar concentration, as a substitute for gelatin. For example, it has the following composition:

| Example 15: Gummy jelly | | |
|---|---|---|
| (Constituents) | (Prior-art Product) | (Product of the Invention) |
| sugar | 35.00 parts | 35.00 parts |
| thick malt syrup | 20.00 parts | 25.00 parts |
| sorbitol | 20.00 parts | 20.00 parts |
| fruit juice (⅕ condensation) | 5.00 parts | 5.00 parts |
| gelatin | 8.00 parts | — |
| low gel strength agar | — | 1.00 part |
| locust | — | 2.00 parts |
| perfume | 0.30 part | 0.30 part |
| coloring matter | 0.05 part | 0.05 part |
| water | 11.65 parts | 11.65 parts |

There are following differences between prior-art gummy jelly and the gummy jelly of the present invention. Gelatin is used in the prior-art gummy jelly. Thus, the jelly melts when the temperature rises in the summer, and the texture varies depending on temperatures. By contrast, the product of the present invention using the agar has no such problems.

Gelatin is a protein and has caloric, whereas the low gel strength agar is dietary fibers of a polysaccharide and is a non-calorie food. If the low gel strength agar is used, a food of a softer texture can be achieved, with no smell of animal protein like gelatin.

Caramel according to this invention contains the low gel strength agar whose gel strength is adjusted to 250 g/cm$^2$ or below at 1.5% agar concentration. For example, it has the following composition:

| Example 16: Caramel | | |
|---|---|---|
| (Constituents) | (Prior-art Product) | (Product of the Invention) |
| sugar | 45.0 parts | 45.0 parts |
| thick malt syrup | 30.0 parts | 30.0 parts |
| sweetened condensed milk | 23.0 parts | 23.0 parts |
| butter | 10.0 parts | 10.0 parts |
| caramel syrup | 3.0 parts | 3.0 parts |
| low gel strength agar | — | 0.6 part |

Example 16: Caramel

| (Constituents) | (Prior-art Product) | (Product of the Invention) |
| --- | --- | --- |
| water | 30.0 parts | 30.0 parts |
| finished product | 100 parts | 100 parts |

The caramel of this invention containing a small amount of low gel strength agar, as compared to the prior-art product, does not easily adhere to the teeth and is not sticky. In addition, even in the summer, it does not soften. Further, if the concentration of the low gel strength agar is increased (e.g. about 5%) and the sugar content is decreased, a healthy caramel with vegetable fibers can be obtained. The same technique is applicable to chewing gum.

Jam according to this invention contains the low gel strength agar whose gel strength is adjusted to 250 g/cm$^2$ or below at 1.5% agar concentration. For example, it has the following composition:

Example 17: Jam

| (Constituents) | (Product of the Invention) |
| --- | --- |
| fruit juice | 40.0 parts |
| water | 51.4 parts |
| sugar | 6.0 parts |
| low gel strength agar | 2.0 parts |
| citric acid | 0.6 part |

A commercially available conventional jam, pectin jam, has stickiness, but the jam of this invention using the low gel strength agar has good flavor release and is not sticky. In addition, the freshness of contained fruits can be enjoyed.

Peanut butter spread according to this invention contains the low gel strength agar whose gel strength is adjusted to 250 g/cm$^2$ or below at 1.5% agar concentration. For example, it has the following composition:

Example 17B: Peanut butter spread

| (Constituents) | (Product of the Invention) |
| --- | --- |
| low gel strength agar | 1.0 part |
| vegetable fat and oils | 30.0 parts |
| corn syrup solid | 10.0 parts |
| skim milk powder | 5.0 parts |
| peanut butter | 5.0 parts |
| emulsifier | 0.6 part |
| salt | 0.4 part |
| water | 48.0 parts |

The peanut butter spread of this invention using the low gel strength agar has good flavor release and makes smooth texture.

Honey spread according to this invention contains the low gel strength agar whose gel strength is adjusted to 250 g/cm$^2$ or below at 1.5% agar concentration. For example, it has the following composition:

Example 18: Honey spread

| (Constituents) | (Product of the Invention) |
| --- | --- |
| low gel strength agar | 2 parts |
| honey | 78 parts |
| water | 20 parts |

The honey spread according to this invention contains low gel strength agar, and it is a margarine-like spread with no webbing properties.

Sauce according to this invention contains the low gel strength agar, whose gel strength is adjusted to 250 g/cm$^2$ or below at 1.5% agar concentration, as a substitute for corn starch. For example, it has the following composition:

Example 19: Sauce

| (Constituents) | (Prior-art Product) | (Product of the Invention) |
| --- | --- | --- |
| vegetable extract paste | 20.0 parts | 20.0 parts |
| sugar | 30.0 parts | 30.0 parts |
| salt | 5.0 parts | 5.0 parts |
| caramel | 0.5 part | 0.5 part |
| vinegar | 15.0 parts | 15.0 parts |
| chemical seasoning | 0.1 part | 0.1 part |
| spice | 1.0 part | 1.0 part |
| corn starch | 1.0 part | — |
| low gel strength agar | — | 1.0 part |
| water | 27.4 parts | 27.4 parts |

Recently, brown Worcestershire sauces which are generally called "sauce" in Japan include not only conventional Worcestershire sauce, middle-thick sauce, and thick sauce, but also various sauces for, "okonomiyaki" (a kind of Japanese pancake). The tastes and texture are widely varied in accordance with purposes of use.

In general, starches such as corn starch is used to make sauces dense, and an additive of tamarind gum, etc. is used as thickening agent. The starch, however, causes the texture to change due to time-based separation or aging, and it is susceptible to microorganismal enzyme decomposition. Further, the use of thickening agent causes webbing. In particular, in the case of thick sauce, thixotropic properties are not exhibited.

By contrast, if the low gel strength agar is used, as in the present invention, special textures can be given to various sauces classified according to purposes of use.

Japanese sauces according to this invention include sauces for fish and shellfish, sauces for meat products and sauces for confectionery. For example, a sauce for meat balls contains the low gel strength agar, whose gel strength is adjusted to 250 g/cm$^2$ or below at 1.5% agar concentration, as a substitute for dogtooth violet starch. For example, it has the following composition:

Example 20: Sauce for meat balls

| (Constituents) | (Prior-art Product) | (Product of the Invention) |
| --- | --- | --- |
| soy sauce | 20 parts | 20 parts |
| water | 29 parts | 34 parts |
| sugar | 30 parts | 30 parts |
| dogtooth violet starch | 6 parts | — |
| thick malt syrup | 9 parts | 9 parts |
| "mirin" (seasoning sweet sake) | 6 parts | 6 parts |
| low gel strength agar | — | 1 part |

If dogtooth violet starch is used, as in the prior-art product, the starch ages and becomes "crumbly" gradually.

By contrast, if the low gel strength agar is used, as in the present invention, the sauce does not age and has good adhesion to meat balls. In addition, the low gel strength agar contributes to flavor release of soy sauce.

Brown sauce according to this invention has following composition:

| Example 20B: Brown sauce | | |
| --- | --- | --- |
| (Constituents) | (Prior-art Product) | (Product of the Invention) |
| wheat flour | 1.6 parts | — |
| water | 59.4 parts | 60.5 parts |
| beef | 15.0 parts | 15.0 parts |
| poultry skin | 5.0 parts | 5.0 parts |
| bacon | 1.0 part | 1.0 part |
| onion | 2.0 parts | 2.0 parts |
| carrot | 1.0 part | 1.0 part |
| tomato | 15.0 parts | 15.0 parts |
| thyme, laurel | optimum | optimum |
| low gel strength agar | — | 0.5 part |

Brown sauce according to this invention improve texture and has good flavor release.

Sauce for "yakitori" or Japanese grilled chicken according to this invention contains the low gel strength agar, whose gel strength is adjusted to 250 g/cm$^2$ or below at 1.5% agar concentration, as a substitute for dogtooth violet starch. For example, it has the following composition:

| Example 21: Sauce for Japanese grilled chicken | | |
| --- | --- | --- |
| (Constituents) | (Prior-art Product) | (Product of the Invention) |
| soy sauce | 40 parts | 40 parts |
| sugar | 10 parts | 10 parts |
| sorbitol | 8 parts | 8 parts |
| "mirin" (seasoning sweet sake) | 7 parts | 7 parts |
| water | 31 parts | 32 parts |
| dogtooth violet starch | 4 parts | 2 parts |
| low gel strength agar | — | 1 part |

Sauce for Japanese grilled chicken needs to have good adhesion and stickiness on meat, when it is grilled after dipped in sauce, and also needs to be free from time-basis change.

Regarding this, the prior-art product contains starch. Thus, sauce is easily removed when the chicken is grilled after it is dipped in the sauce, and also the sauce is easily scorched. Further, when the sauce is marketed in a packed state, the starch in the sauce ages with the passing of time, resulting in water removal.

By contrast, the product of the present invention using the low gel strength agar has good flavor release and good adhesion on the meat.

Pizza sauce according to this invention has the following composition:

| Example 21B: Pizza sauce | |
| --- | --- |
| (Constituents) | (Product of the Invention) |
| onion | 12.5 parts |
| olive oil | 3.8 parts |
| garlic | 2.5 parts |
| boiled tomato | 63.7 parts |
| tomato paste | 14.0 parts |
| oregano, basil, laurel | optimum |
| sugar | 3.0 parts |
| low gel strength agar | 0.5 part |

Pizza sauce according to this invention can spread easily and not drip down.

Noodles according to this invention contain the low gel strength agar, whose gel strength is adjusted to 250 g/cm$^2$ or below at 1.5% agar concentration. For example, cooled noodles have the following composition:

| Example 22: Cooled noodles | | |
| --- | --- | --- |
| (Constituents) | (Prior-art Product) | (Product of the Invention) |
| wheat flour | 75.0 parts | 75.0 parts |
| brine powder | 0.7 part | 0.4 part |
| albumen powder | 0.5 part | 0.5 part |
| salt | 1.0 part | 0.5 part |
| water | 22.8 parts | 22.5 parts |
| low gel strength agar | — | 1.0 part |
| coloring matter | — | 0.1 part |

The noodles according to this invention contain the low gel strength agar, and therefore the noodles have more "resiliency" and "smoothness" than the prior-art product. In particular, since the cooled noodles match the gelatinizing force of agar, texture improvement effect is great. In addition, since the amount of brine can be reduced, healthy cooled noodle is obtained.

A similar example is "cupped" (packed in a cup) uncooked Chinese noodles, by which boiled noodles can be preserved for a long time. The "cupped" uncooked Chinese noodles according to this invention contain the low gel strength agar whose gel strength is adjusted to 250 g/cm$^2$ or below at 1.5% agar concentration. For example, the noodles have the following composition:

| Example 23: "Cupped" uncooked Chinese noodles | |
| --- | --- |
| (Constituents) | (Product of the Invention) |
| wheat flour | 73.0 parts |
| brine powder | 0.1 part |
| albumen powder | 1.0 part |
| salt | 0.5 part |
| water | 19.3 parts |
| low gel strength agar | 2.0 parts |
| coloring matter | 0.1 part |
| citric acid solution | 5.0 parts |

Recently, in the industry of precooked Chinese noodles, uncooked noodles in the "cupped" condition have been gradually marketed, since consumers prefer "uncooked" noodles to "dried" noodles. This trend began with "udon" noodles and "soba" noodles (both Japanese noodles), and now uncooked Chinese noodles have been sold. Although the texture of uncooked "udon" and "soba" are satisfactory, there is much to be desired in the uncooked Chinese noodles.

The reason is that in order to keep microorganismal stability, the "soba" noodles and Chinese noodles are processed with acidifier, such as citric acid and phytin acid, to the acid side (about pH4) for long-time preservation.

Specifically, in the case of "udon" noodles whose "resiliency" is obtained by salt and gluten in wheat flour, or in the case of "soba" noodles having texture of only buckwheat flour and wheat flour, there is not so much variation in texture even if these noodles are processed to the acid pH side by citric acid, etc. However, in the case of Chinese noodles, the "resiliency", the color (yellow) and flavor are created by the reaction between alkali side brine and wheat flour. Thus, if the Chinese noodles are processed to the acid side, the system of needles is damaged and rendered "crumbly".

By contrast, if the low gel strength agar is used, as in the present invention, good result is obtained. Regarding the composition of Example 23, a small amount of brine was added to wheat flour for the purpose of flavoring. Then, the pH of the resultant was adjusted by citric acid solution. After the noodles were boiled, the adhesion between noodles was prevented by using oil, and subjected to secondary sterilization.

The thus obtained "cupped" uncooked Chinese noodles according to this invention have less "crumbly" texture than the prior-art product, and "boiling expansion" (expansion of noodles during boiling) is also less than the prior-art product. The texture-improved noodles using the low gel strength agar are applicable not only to Chinese noodles (including steamed noodles for "chow mein"), but also to "udon", "soba", fine noodles, spaghetti, etc.

Bread according to this invention contains the low gel strength agar whose gel strength is adjusted to 250 g/cm$^2$ or below at 1.5% agar concentration. For example, it has the following composition:

Example 24: Bread

| (Constituents) | (Prior-art Product) | (Product of the Invention) |
|---|---|---|
| strong wheat flour | 53.0 parts | 53.0 parts |
| yeast | 1.8 parts | 1.8 parts |
| high-grade white sugar | 3.8 parts | 3.7 parts |
| salt | 0.8 part | 0.8 part |
| yolk and albumen | 6.3 parts | 6.3 parts |
| margarine | 3.7 parts | 3.7 parts |
| water | 30.7 parts | 29.7 parts |
| low gel strength agar | — | 1.0 part |

Since the low gel strength agar is used in the bread of the invention, the bread is softer than the prior-art product and is less aged. A variation between products in the manufacturing process can be reduced, and bread can be stably manufactured.

Icing according to this invention contains the low gel strength agar whose gel strength is adjusted to 250 g/cm$^2$ or below at 1.5% agar concentration. For example, it has the following composition:

Example 24B: Icing

| (Constituents) | (Product of the Invention) |
|---|---|
| low gel strength agar | 0.6 part |
| Emulsifier | 0.4 part |
| Starch | 0.8 part |
| Sucrose, granulated | 15.0 parts |
| Icing sugar | 73.0 parts |
| Water | 10.0 parts |

Icing of this invention using the low gel strength agar has good solubility and easily boil down. It has good water-retaining and shape-retention properties.

Rice according to this invention contains, as vegetable fibers, the low gel strength agar whose gel strength is adjusted to 250 g/cm$^2$ or below at 1.5% agar concentration. For example, the following amount of additive is mixed in ordinary rice:

Example 25: Rice

| (Constituents) | (Product of the Invention) |
|---|---|
| rice | 1.8 liters |

Example 25: Rice

| (Constituents) | (Product of the Invention) |
|---|---|
| low gel strength agar | 3.0 g |

If the low gel strength agar is added, as in the present invention, the rice has good gloss and stickiness. This advantage is greater with older rice. Thus, a recent demand for high-quality rice can be satisfied.

If a coating of low gel strength agar is applied to "wash less" rice developed to simplify washing of rice before cooking, time-basis degradation of rice can be prevented. This advantage is obtained by making use of the feature of the low gel strength agar in which it has low viscosity and can be dissolved at high concentration.

A dietary fiber-containing beverage according to this invention contains, as dietary fibers, the low gel strength agar whose gel strength is adjusted to 250 g/cm$^2$ or Below at 1.5% agar concentration. For example, the beverage has the following composition:

Example 26: Dietary fiber-containing beverage

| (Constituents) | (Product of the Invention) |
|---|---|
| low gel strength agar | 2.0 parts |
| liquid sugar | 8.0 parts |
| fruit juice | 20.0 parts |
| perfume | 0.5 part |
| water | 69.0 parts |
| acidifier | 0.5 part |

Agar contains a largest amount of dietary fibers of all foods. If agar is contained in a beverage, dietary fibers can be taken in only by drinking the beverage. However, since conventional agar has a strong gelatinizing force, it must be used at a concentration of 0.1% or less in order to prevent gelatinization. This concentration is very low. Thus, a beverage with such a low agar concentration cannot be said to have sufficient dietary fibers.

By contrast, even if a large amount of low gel strength agar is contained, as in the present invention, gelatinization does not occur and a beverage with sufficient dietary fibers can be achieved. In addition, by adjusting the gel strength of the low gel strength agar used in the beverage, various types of beverages (from "nectar" to "light" beverages) with a wide rang of textures can be achieved. In particular, light and non-sticky texture peculiar to agar can be achieved.

Japanese rice cakes according to the invention include "kashiwa-mochi" (rice cake wrapped in an oak leaf), "daifuku-mochi" (rice cake stuffed with bean jam), "sakura-mochi", "suama", "yubeshi", "dango", "gyuhi", cut rice cakes. The rice cake according to this invention contains the low gel strength agar whose gel strength is adjusted to 250 g/cm$^2$ or below at 1.5% agar concentration. For example, "kashiwa-mochi" has the following composition:

Example 2.7: "kashiwa-mochi"

| (Constituents) | (Prior-art Product) | (Product of the Invention) |
|---|---|---|
| quality rice flour | 54.0 parts | 52.5 parts |
| salt | 0.3 part | 0.3 part |
| dogtooth violet starch | 2.7 parts | 2.7 parts |
| hot water (60° C.) | 43.0 parts | 43.0 parts |

-continued

Example 2.7: "kashiwa-mochi"

| (Constituents) | (Prior-art Product) | (Product of the Invention) |
|---|---|---|
| low gel strength agar | — | 1.5 part |

Conventional "kashiwa-mochi" contains mainly quality rice flour. If the "kashiwa-mochi" is prepared by steaming and kneading according to the above recipe of the prior-art product, it ages easily and its texture varies easily.

By contrast, the "kashiwa-mochi" of this invention containing the low gel strength agar does not easily age, and also its texture does not easily change.

The low gel strength agar may also be contained in other rice cakes such as "shoyo-manju", "sake-manju", "keiyo-manju", "kuzu-manju", "mushi-manju", "Chinese-manju", "oyaki", "uiro", and the same aging-prevention effect can be obtained.

Foods using the low gel strength agar of the present invention are not limited to the above examples. The gel strength of the low gel strength agar used in the present invention is lowered in advance by acid and heat, and then it is contained in foods. However, alternatively, a normal strength agar may be contained in foods in advance, and in the foods manufacturing process the normal agar may be processed by acid and heated, so that the gel strength of the agar may lower as well as that of the low gel strength agar as mentioned above. The low gel strength agar of the invention includes such agar.

Conventionally, cosmetics such as milky lotion, cream, shampoo, pack and tooth powder contain, as thickening agent, tragacanth gum, karaya gum, pectin, sodium alginate, carrageenan, CMC, MC, PVP, etc.

Recently, there is a demand for "non-color", "non-perfume" cosmetics, and natural materials are used for cosmetics. For example, there is an attempt to use agar extracted from seaweed as thickening agent. The reason for this is that agar contains effective components such as minerals and it is thought to become more natural material for cosmetics.

However, conventional agar has a strong gelatinizing force, as stated above. Thus, if it is used at high concentration, fluidity is insufficient. When it is actually contained in cosmetics, it is difficult to maintain the liquid- or cream-phase. If the conventional agar is used at low concentration in order to avoid this, the agar content decreases and the functions (thickening properties, permeability, etc.) peculiar to agar cannot be exhibited. The low gel strength agar of the present invention has no such problems, and it can be contained in cosmetics with good advantages expected. Examples of the cosmetics according to this invention will now be described.

In Example 28, 0.5 part of low gel strength agar is contained in 100 parts of lotion.

| Example 28: Lotion | |
|---|---|
| low gel strength agar | 0.5 part |
| ethanol | 5 parts |
| glycerine | 5 parts |
| lemon extract | 2 parts |
| water | 87.5 parts |
| (total) | (100 parts) |

The lotion obtained by this composition is superior to lotion containing conventional thickening agent, in advantages of providing the skin with moisture, smoothing the skin, and cleaning the skin.

In Example 29, 3 parts of low gel strength agar is contained in 100 parts of a packing agent.

| Example 29: Packing agent | |
|---|---|
| low gel strength agar | 3 parts |
| glycerine | 5 parts |
| ethanol | 10 parts |
| perfume | suitable amount |
| antiseptic | suitable amount |
| water | 82 parts |
| (total) | (100 parts) |

The packing agent obtained by this composition is superior to a packing agent containing conventional thickening agent, in advantages of providing the skin with moisture, smoothing the skin, and cleaning the skin.

In Example 30, 1 part of low gel strength agar is contained in 100 parts of shampoo.

| Example 30: Shampoo | |
|---|---|
| low gel strength agar | 1 part |
| lauryl sulfate triethanolamine | 15 parts |
| lauryl sulfate diethanolamide | 2 parts |
| perfume | suitable amount |
| coloring matter | suitable amount |
| water | 82 parts |
| (total) | (100 parts) |

The shampoo obtained by this composition is superior to shampoo containing conventional thickening agent, in advantages of providing the skin with moisture, smoothing the skin, and cleaning the skin.

The cosmetics of the present invention are not limited to the above examples, and are applicable to creams, tooth powders, etc. In addition, the concentration of the used low gel strength agar is not limited to the values shown in the examples.

What is claimed is:

1. A process for producing a food material exhibiting unique desirable properties not otherwise present in said food materials, comprising:

treating agar with acid to reduce the molecular weight of the agar components of manufactured agar materials to produce low gel strength agar;

terminating the effect of the acid in a neutralization treatment step, thereby adjusting the molecular weight of the product to a degree such that when the agar is present in water at a concentration of 1.5%, said agar has a gel strength in the range between 10 to 250 $g/cm^2$; and combining the resulting low gel strength agar with a food material.

2. The process according to claim 1, further comprising drying the low gel strength agar product to obtain a dry agar material.

3. A process for producing a food material exhibiting unique desirable properties not otherwise present in said food material, comprising:

extracting agar components from seaweeds serving as the raw materials of agar to manufacture normal agar;

treating the so-extracted normal agar with acid to reduce the molecular weight of the normal agar components to produce low gel strength agar;

neutralizing the acid to terminate its effect, thereby adjusting the molecular weight of the low gel strength agar to a degree such that when the agar is present in water at a concentration of 1.5%, the agar has a gel strength in the range between 10 to 250 g/cm$^2$; and combining the resulting low gel strength agar with a food material.

4. The process according to claim 3, wherein the seaweeds are subjected to alkali treatment to increase coagulation properties prior to the extraction step.

5. The process according to claim 4, including the step wherein the extracted agar is filtered and then cooled, thereby producing a gelatinized intermediate product.

6. The process according to claim 5, wherein the acid treatment of the agar is controlled to produce an agar having a low gel strength of 200 g/cm$^2$ at 1.5% agar concentration.

7. The process according to claim 3, wherein the agar is subjected to drying and pulverizing treatments prior to the acid treatment.

8. The process according to claim 3, further comprising drying the low gel strength agar to obtain a dry product.

9. The process according to claim 3, wherein the acid treatment of the agar is controlled to produce an agar having a low gel strength of 200 g/cm$^2$ at 1.5% agar concentration.

10. The process according to claim 3, wherein the acid treatment of the agar is controlled to produce an agar having a low gel strength of 60 g/cm$^2$ at 1.5% agar concentration.

* * * * *